(12) United States Patent
Verbeke et al.

(10) Patent No.: US 11,530,188 B2
(45) Date of Patent: Dec. 20, 2022

(54) CATALYSTS FOR MAKING OXAZOLIDINONE MATERIALS

(71) Applicant: Huntsman International LLC, The Woodlands, TX (US)

(72) Inventors: Hugo Verbeke, Wilsele (BE); Elisabeth Els Mercier, Overwinden (BE); Lies Bonami, Aalter (BE); Peter Karel Joris Bosman, Herselt (BE); Giacomo Giannini, Tervuren (BE)

(73) Assignee: Huntsman International LLC, The Woodlands, TX (US)

( * ) Notice: Subject to any disclaimer, the term of this patent is extended or adjusted under 35 U.S.C. 154(b) by 112 days.

(21) Appl. No.: 16/754,278

(22) PCT Filed: Oct. 10, 2018

(86) PCT No.: PCT/EP2018/077593
§ 371 (c)(1),
(2) Date: Apr. 7, 2020

(87) PCT Pub. No.: WO2019/081210
PCT Pub. Date: May 2, 2019

(65) Prior Publication Data
US 2020/0308124 A1    Oct. 1, 2020

(30) Foreign Application Priority Data

Oct. 27, 2017 (EP) .................... 17198780

(51) Int. Cl.
| | |
|---|---|
| *C07D 263/22* | (2006.01) |
| *B01J 27/26* | (2006.01) |
| *C08G 18/00* | (2006.01) |
| *C08G 18/22* | (2006.01) |
| *C08G 18/76* | (2006.01) |

(52) U.S. Cl.
CPC ............ *C07D 263/22* (2013.01); *B01J 27/26* (2013.01); *C08G 18/003* (2013.01); *C08G 18/222* (2013.01); *C08G 18/7671* (2013.01)

(58) Field of Classification Search
CPC ...... C07D 263/22; B01J 27/26; C08G 18/003; C08G 18/222; C08G 18/7671
See application file for complete search history.

(56) References Cited

FOREIGN PATENT DOCUMENTS

| | | | |
|---|---|---|---|
| DE | 19742978 | 4/1999 | |
| EP | 862947 | 9/1998 | |
| WO | 1986/06734 | 11/1986 | |
| WO | 2014/076024 | 5/2014 | |
| WO | WO-2014076024 A1 * | 5/2014 | ........... C08G 18/003 |
| WO | 2015/173111 A1 | 11/2015 | |

OTHER PUBLICATIONS

International Search Report received in corresponding PCT Application PCT/EP2018/077593 completed Jan. 9, 2019 and dated Jan. 22, 2019.
Written Opinion received in corresponding PCT Application PCT/EP2018/077593 completed Jan. 9, 2019 and dated Jan. 22, 2019.

* cited by examiner

*Primary Examiner* — Rabon A Sergent
(74) *Attorney, Agent, or Firm* — Huntsman International LLC

(57) ABSTRACT

A catalyst composition comprising at least a catalyst compound selected from multi metal cyanide compounds for the selective production of oxazolidinone compounds by reacting an isocyanate compound with an epoxide compound and oxazolidinone comprising materials obtained using said catalyst compound.

7 Claims, 1 Drawing Sheet

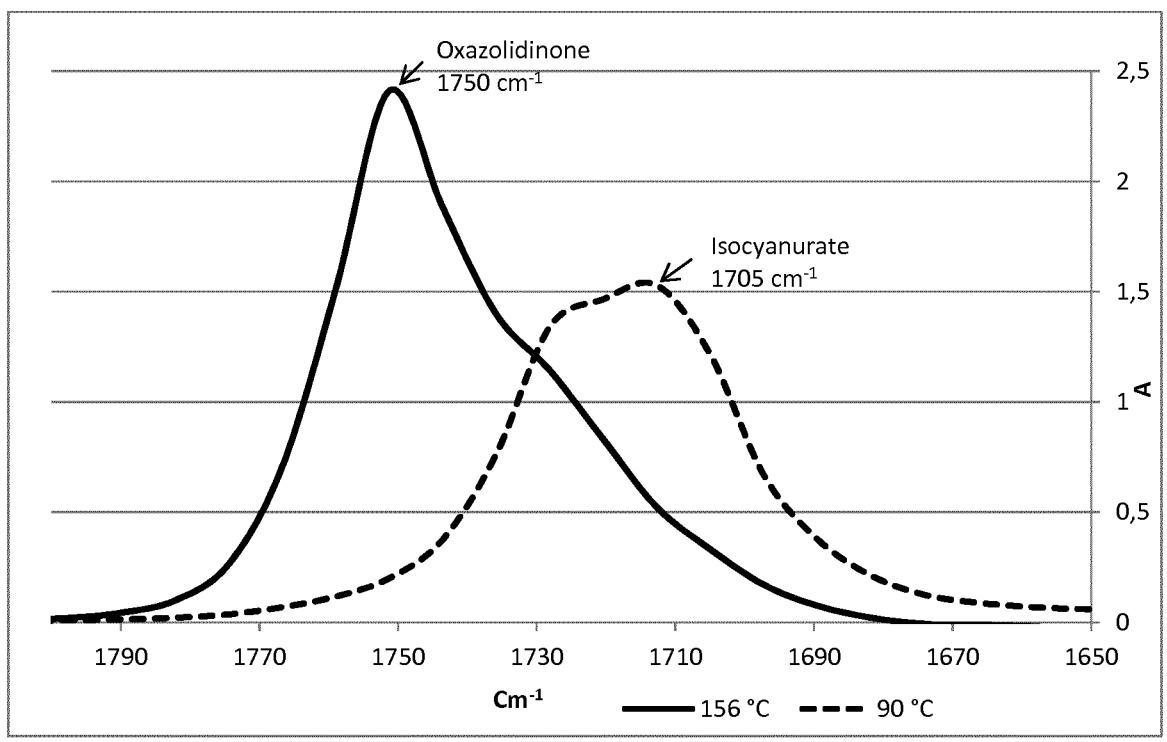

CATALYSTS FOR MAKING OXAZOLIDINONE MATERIALS

CROSS-REFERENCE TO RELATED APPLICATIONS

This application is the National Phase of International Application PCT/EP2018/077593 filed Oct. 10, 2018 which claims priority to EP App. Ser. No. 17198780.3 filed Oct. 27, 2017. The noted applications are incorporated herein by reference.

FIELD OF INVENTION

The present invention is related to a catalyst composition comprising at least a catalyst compound selected from multi metal cyanide compounds for the selective production of oxazolidinone compounds by reacting an isocyanate compound with an epoxide compound and to the oxazolidinone comprising materials obtained using said catalyst compound.

The invention further relates to a method for the production of oligo-oxazolidinone and/or poly-oxazolidinone compounds, comprising the step of reacting an isocyanate compound with an epoxide compound in the presence of the catalyst according to the invention.

Further the present invention is related to a process for preparing oxazolidinone comprising materials.

BACKGROUND

Oxazolidinone groups are known to be more thermally stable than polyurethane groups and could therefore result in thermoplastic materials having better thermal resistance and fire properties and higher Tg than standard thermoplastic polyurethane (TPU).

It is well known to react an epoxide compound with an isocyanate compound in order to form an oxazolidinone compound. Such reactions are generally carried out in the presence of a catalyst. Typical catalysts for this reaction include lithium bromide, quaternary ammonium salts, tertiary amines, Lewis acids, such as aluminum chloride, complexes of these Lewis acids with a Lewis base, and similar materials.

The reaction of an epoxide compounds with isocyanate compounds leads to the formation of oxazolidinone structures according to following reaction:

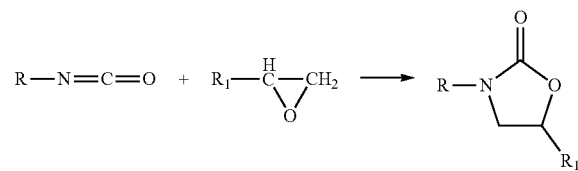

In a similar manner, polyoxazolidinones can be prepared by reacting a poly-epoxide (i.e. a compound having at least two oxirane groups) with a poly isocyanate (i.e. a compound having at least two isocyanate groups). In particular, the reaction of di-epoxide compounds and di-isocyanate compounds may lead to the formation of oxazolidinones.

However, whereas the reaction of mono-epoxide compounds and mono-isocyanate compounds to form oxazolidinone compounds proceeds relatively cleanly and in good yield, the corresponding reaction between higher functionality epoxide compounds and isocyanate compounds results in the formation of substantial quantities of undesirable by-products. The major by-products are polyethers prepared by the homo-polymerization of the polyepoxide and isocyanurates formed by the trimerization of the polyisocyanate. according to below reaction.

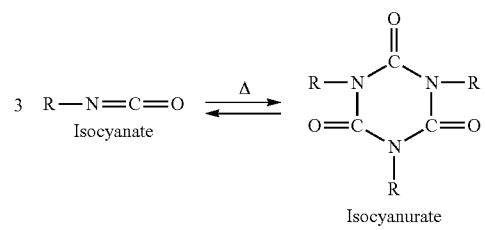

Of these, the trimerization reaction is particularly disadvantageous since the trimerization of polyisocyanates leads to the formation of very high functionality materials which give rise to very highly cross-linked, brittle polymers. Unfortunately, most state of the art catalysts conventionally used in preparing (poly) oxazolidinone compounds do not selectively catalyze the oxazolidinone reaction, and substantial quantities of isocyanurates are formed. Generally, the polyoxazolidinone prepared by processes known in the art starting from higher functionality epoxide compounds and isocyanate compounds contains significant amounts of isocyanurates.

For this reason, it would be desirable to provide a process whereby polyepoxide compounds and polyisocyanate compounds are reacted to form a (poly) oxazolidinone comprising material containing almost no or relatively small quantities of trimerized isocyanates and to achieve a high (chemo) selectivity towards the oxazolidinone formation.

WO 86/06734 discloses a process for preparing a polyoxazolidinone by reacting together a polyepoxide and a polyisocyanate. The process is characterized by reacting said polyepoxide and polyisocyanate in the presence of a catalytic amount of an organoantimony iodide. In this process, the oxazolidinone forming reaction proceeds much more rapidly than the trimerization reaction of the polyisocyanate or the homopolymerization of the polyepoxide. As a result, the product polymer or polymer precursor may contain only small proportions of isocyanurates. The catalyst used is however highly toxic and high amounts of catalyst (0.3 up to 20 moles of antimony catalyst per 100 moles of polyepoxide) are required to obtain the claimed selectivity.

WO 86/06734 A1 discloses a process for the preparation of polyisocyanurate-based polyoxazolidinone polymers containing relatively small proportions of trimerized polyisocyanates. The catalysts used are phosphonium based catalysts such as methyl tributyl phosphonium iodide.

WO2015173111 discloses use of particular onium salts as oxazolidinone catalyst. The use of such special onium salts leads to a high rate in the reaction of isocyanates and epoxides and enables the production of the oxazolidinone compounds with high chemo selectivity.

WO2014076024 discloses a method for the production of oxazolidinone compounds, comprising the step of slowly reacting an isocyanate compound with an epoxide compound in the presence of a Lewis acid catalyst. The oxazolidinone compound obtained has a molar ratio of the oxazolidinone compound to isocyanurate by-product of ≥85/15.

GOAL OF THE INVENTION

It is the goal of the invention to improve the processing for making oxazolidinone compounds or oxazolidinone comprising materials starting from isocyanate compounds and epoxide compounds.

The goal is to improve the oxazolidinone formation and to achieve selective catalysis of isocyanate compounds and epoxide compounds to form oxazolidinone compounds thereby minimizing or even avoiding the formation of polyisocyanurates. A higher oxazolidinone conversion will lead to 100% pure or almost pure oxazolidinone materials.

It is a further goal to make oxazolidinone intermediate materials which contain NCO functionality and/or epoxide functionality and which can be used in the manufacture of resins and plastics.

Surprisingly we have found an oxazolidinone selective catalyst which has significant high selectivity towards oxazolidinone formation, which has improved reaction time and which is effective in low concentrations compared to above described state of the art oxazolidinone catalysts. As a result of the higher selectivity, materials can be fabricated with almost no polyisocyanurates (PIR).

SUMMARY OF THE INVENTION

According to the invention, a method and novel catalyst is disclosed for the production of oxazolidinone compounds. Said method comprising combining and mixing at a temperature in the range 130-200° C. at least following compounds to form a reactive mixture:

- an isocyanate composition comprising at least one isocyanate compound;
- an epoxide composition comprising at least one epoxide compound;
- an oxazolidinone catalyst composition comprising at least an oxazolidinone catalyst compound selected from multi metal cyanide compounds corresponding to the formula [I]

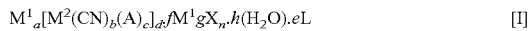

wherein $M^1$ is a metal ion selected from the group consisting of $Zn^{2+}$, $Fe^{2+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W4^+$, $W^{6+}$, $Cr^{2+}$, $Cr^{3+}$, $Cd^{2+}$, $Hg^{2+}$, $Pd^{2+}$, $Pt^{2+}$ $V^{2+}$, $Mg^{2+}$, $Ca^{2+}$, $Ba^{2+}$, $Cu^2+$ $M^2$ is a metal ion selected from the group consisting of $Fe^{2+}$, $Fe^{3+}$, $Co^{3+}$, $Mn^{2+}$, $Co^{2+}$, $Mn^{3+}$, $V^{4+}$, $V^{5+}$, $Cr^{2+}$, $Cr^{3+}$, $Rh^{3+}$, $Ru^{2+}$, $Ir^{3+}$ $M^1$ and $M^2$ can be identical or different.

A is an anion selected from the group consisting of halide, hydroxide, sulfate, carbonate, cyanide, thiocyanate, isocyanate, cyanate, carboxylate, oxalate and nitrate, L is a water-miscible ligand selected from the group consisting of alkyls, aldehydes, ketones, ethers, polyethers, esters, ureas, amides, nitriles, lactones, lactams and sulfides, a, b, c, d, g and n are chosen so that the compound is electrically neutral, a is preferably 1, 2, 3 or 4, b is preferably 4, 5 or 6 and c preferably has the value 0 e is the coordination number of the ligand or 0, f is a fraction or integer greater than or equal to 0, and h is a fraction or integer greater than or equal to 0.

According to embodiments of the invention, the multi metal cyanide compounds are corresponding to formula [II]:

wherein

L=tBuOH or 1,2-dimethoxyethane e is the coordination number of the ligand or 0, f is a fraction or integer greater than or equal to 0, and h is a fraction or integer greater than or equal to 0.

According to preferred embodiments, the multi metal cyanide compounds are corresponding to formula [III] and comprising mainly structure [III] below.

[III]

[III]

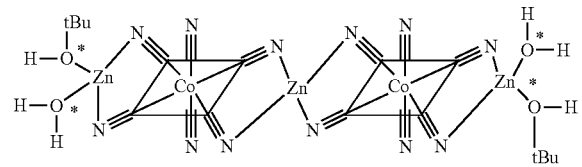

According to embodiments of the invention, the temperature of the reaction to form oxazolidinones is from 135 to 160° C.

According to embodiments of the invention, the amount of multi metal cyanide compounds in the reactive mixture is preferably from 5 to 5000 parts by weight per million (ppm) parts by weight of the reactive mixture, preferably in an amount of at least 10 ppm up to about 500 ppm, more preferably in an amount from 25 to 200 ppm by weight of the reactive mixture.

According to embodiments of the invention, the isocyanate composition is added to the epoxide composition in a continuous or step-wise manner with two or more individual addition steps in the step-wise addition wherein in each individual addition step the amount of isocyanate compound added is <50 weight % of the total weight of isocyanate compounds to be added.

According to embodiments of the invention, the ratio of isocyanate compounds to epoxide compounds is from about 3:0.1 to about 0.1:3, preferably in the range 1:3 up to 3:1 isocyanate (NCO) equivalents to epoxide equivalents (NCO: epoxide).

According to embodiments of the invention, the ratio of isocyanate compounds to epoxide compounds is greater than 1 (NCO:epoxide).

According to embodiments of the invention, the ratio of isocyanate compounds to epoxide compounds is smaller than 1 (NCO:epoxide).

According to embodiments of the invention, the ratio of isocyanate compounds to epoxide compounds is about 1.

According to embodiments of the invention, the isocyanate compounds in the isocyanate composition are selected from a toluene diisocyanate, a methylene diphenyl diisocyanate or a polyisocyanate composition comprising a methylene diphenyl diisocyanate or a mixture of such polyisocyanates.

Further according to the invention, an oxazolidinone compound obtained by the method according to the invention is disclosed using an isocyanate compound with two NCO groups per molecule and an epoxide compound with two epoxy groups per molecule, comprising at least one unit derived from the isocyanate compound and at least two units derived from the epoxide compound.

According to embodiments of the invention, oxazolidinone compound obtained by the method according to the invention is comprising at least one terminal epoxide and/or isocyanate group or comprising at least one terminal group which is non-reactive towards epoxide and/or isocyanate groups.

Furthermore, the use of compounds according to the general formula (I) for the manufacture of oligomeric or polymeric oxazolidinone compounds is disclosed.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention.

Definitions and Terms

In the context of the present invention the following terms have the following meaning:
1) The word "average" refers to number average unless indicated otherwise.
2) "Oxazolidinone catalyst" as used herein refers to a catalyst being able to catalyse (promote) the formation of oxazolidinone groups from (poly) isocyanate compounds and (poly) epoxide compounds. This means that isocyanates compounds can react with epoxide compounds to form macromolecules with oxazolidinone structures.
3) "Oxazolidinone intermediate material" according to the present invention refers to a material composition obtained by reacting (poly) isocyanate compounds with (poly) epoxide compounds in the presence of at least the oxazolidinone catalyst of the invention wherein said material has remaining free iso-reactive groups (e.g. epoxide-reactive groups) and/or free NCO groups or alternatively wherein said material has remaining free epoxide-reactive groups.
4) "Epoxide compounds" are meant to denote mono-epoxide compounds, poly-epoxide compounds (having two or more epoxide groups) and epoxide terminated prepolymers. The term "mono-epoxide compound" is meant to denote epoxide compounds having one epoxy group. The term "poly-epoxide compound" is meant to denote epoxide compounds having at least two epoxy groups. The term "di-epoxide compound" is meant to denote epoxide compounds having two epoxy groups.
5) "Isocyanate compound" is meant to denote mono-isocyanate compounds, polyisocyanate compounds (having two or more NCO groups), NCO-terminated biuret, isocyanurates, carbamates and NCO-terminated prepolymers. The term "mono-isocyanate compound" is meant to denote isocyanate compounds having one isocyanate group. The term "polyisocyanate compound" is meant to denote isocyanate compounds having at least two isocyanate groups. The term "di-isocyanate compound" is meant to denote polyisocyanate compounds having two isocyanate groups.

DETAILED DESCRIPTION

The present invention will be described with respect to particular embodiments. It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

It is to be understood that although preferred embodiments and/or materials have been discussed for providing embodiments according to the present invention, various modifications or changes may be made without departing from the scope and spirit of this invention.

The present invention relates to oxazolidinone catalyst compounds, a catalyst composition and a process for making oxazolidinone comprising materials as well as oxazolidinone intermediate materials.

The oxazolidinone catalyst compounds according to the invention are selected from one or more multi metal cyanide compounds, also referred to as double metal cyanide (DMC) compounds. Said multi metal cyanide compounds correspond to the formula [I]:

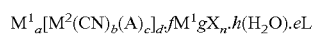  [I]

wherein
M¹ is a metal ion selected from the group consisting of Zn²⁺, Fe²⁺, Co³⁺, Ni²⁺, Mn²⁺, Co²⁺, Sn²⁺, Pb²⁺, Mo⁴⁺, Mo⁶⁺, Al³⁺, V⁴⁺, V⁵⁺, Sr²⁺, W⁴⁺, W⁶⁺, Cr²⁺, Cr³⁺, Cd²⁺, Hg²⁺, Pd², Pt²⁺ V²⁺, Mg²⁺, Ca²⁺, Ba²⁺, Cu²⁺

M² is a metal ion selected from the group consisting of Fe²⁺, Fe³⁺, Co³⁺, Mn²⁺, Co²⁺, Mn³⁺, V⁴⁺, V⁵⁺, Cr²⁺, Cr³⁺, Rh³⁺, Ru²⁺, Ir³⁺

M¹ and M² can be identical or different.

A is an anion selected from the group consisting of halide, hydroxide, sulfate, carbonate, cyanide, thiocyanate, isocyanate, cyanate, carboxylate, oxalate and nitrate, L is a water-miscible ligand selected from the group consisting of alkyls, aldehydes, ketones, ethers, polyethers, esters, ureas, amides, nitriles, lactones, lactams and sulfides, a, b, c, d, g and n are chosen so that the compound is electrically neutral, a is preferably 1, 2, 3 or 4, b is preferably 4, 5 or 6 and c preferably has the value 0 e is the coordination number of the ligand or 0, f is a fraction or integer greater than or equal to 0, and h is a fraction or integer greater than or equal to 0.

The multi metal cyanide compounds used as oxazolidinone catalyst according to the present invention may be prepared by means of generally known methods by combining the aqueous solution of a water-soluble metal salt with the aqueous solution of a hexacyanometalate compound, in particular a salt or an acid, hereinafter also referred to as starting solutions, and, if desired, adding a water-soluble ligand thereto during or after the starting solutions have been combined. Such catalysts and their preparation are described, for example, in EP 862,947 and DE 197,42, 978.

The multi metal cyanide compounds are those compounds in whose preparation the corresponding acids are used as cyanometalate compound. The multi metal cyanide compounds preferably have a particle size in the range from 0.1 to 100 μm.

A particular preferred multi metal cyanide compound corresponds to following formula [II]:

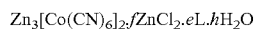

$$Zn_3[Co(CN)_6]_2.fZnCl_2.eL.hH_2O \qquad [II]$$

wherein

L=tBuOH or 1,2-dimethoxyethane e is the coordination number of the ligand or 0, f is a fraction or integer greater than or equal to 0, and h is a fraction or integer greater than or equal to 0.

For use in the present invention the preferred multi metal cyanide compound corresponds to above formula [II] comprises mainly compounds according to the following formula [III] and comprising mainly structure [III] below.

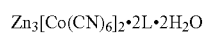

$$Zn_3[Co(CN)_6]_2 \cdot 2L \cdot 2H_2O \qquad [III]$$

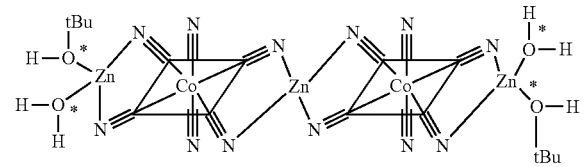

The present invention further discloses an oxazolidinone catalyst composition, said composition comprising at least a catalyst compound selected from one or more multi metal cyanide compounds according to the first aspect of the invention. The multi metal cyanide compounds should be present in the oxazolidinone catalyst composition in a catalytically effective amount.

According to embodiments, the oxazolidinone catalyst composition according to the invention may further comprise a solvent.

According to embodiments, the oxazolidinone catalyst composition according to the invention may further comprise optionally one or more surfactants, one or more flame retardants, water, one or more antioxidants, one or more auxiliary blowing agents, one or more urethane catalysts, one or more auxiliary oxazolidinone catalysts (other than the oxazolidinone catalyst compound according to the invention), or combinations thereof.

Using the catalyst compound according to the invention as oxazolidinone catalyst compound will give rise to production of oxazolidinone compounds with high purity when combined with sufficient amounts of isocyanate compounds and epoxide compounds.

The invention therefore relates to a process for making oxazolidinone compounds and oxazolidinone comprising materials. Said process comprising combining and mixing at a temperature in the range 130-200° C. at least following compounds to form a reactive mixture:

an isocyanate composition comprising at least one isocyanate compound;

an epoxide composition comprising at least one epoxide compound;

an oxazolidinone catalyst composition comprising at least an oxazolidinone catalyst compound selected from multi metal cyanide compounds corresponding to the formula [I]

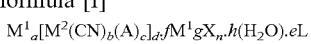

$$M^1_a[M^2(CN)_b(A)_c]_d.fM^1gX_n.h(H_2O).eL \qquad [I]$$

wherein $M^1$ is a metal ion selected from the group consisting of $Zn^{2+}$, $Fe^{2+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W4^+$, $W^{6+}$, $Cr^{2+}$, $Cr^{3+}$, $Cd^{2+}$, $Hg^{2+}$, $Pd^{2+}$, $Pt^{2+}$ $V^{2+}$, $Mg^{2+}$, $Ca^{2+}$, $Ba^{2+}$, $Cu^2$ $M^2$ is a metal ion selected from the group consisting of $Fe^{2+}$, $Fe^{3+}$, $Co^{3+}$, $Mn^{2+}$, $Co^{2+}$, $Mn^{3+}$, $V^{4+}$, $V^{5+}$, $Cr^{2+}$, $Cr^{3+}$, $Rh^{3+}$, $Ru^{2+}$, $Ir^{3+}$ $M^1$ and $M^2$ can be identical or different.

A is an anion selected from the group consisting of halide, hydroxide, sulfate, carbonate, cyanide, thiocyanate, isocyanate, cyanate, carboxylate, oxalate and nitrate, L is a water-miscible ligand selected from the group consisting of alkyls, aldehydes, ketones, ethers, polyethers, esters, ureas, amides, nitriles, lactones, lactams and sulfides, a, b, c, d, g and n are chosen so that the compound is electrically neutral, a is preferably 1, 2, 3 or 4; b is preferably 4, 5 or 6 and c preferably has the value 0 e is the coordination number of the ligand or 0, f is a fraction or integer greater than or equal to 0, and h is a fraction or integer greater than or equal to 0.

According to embodiments, the process for making oxazolidinone compounds thereby using the oxazolidinone catalyst composition according to the invention is performed by combining the catalyst composition, the isocyanate composition and the epoxide composition and heating the resulting mixture to a temperature sufficient to form oxazolidinones. The temperature of the reaction mixture should be above 120° C., from 130° C. to 200° C., preferably from 135° C. to 160° C., more preferably above 150° C. The formation of oxazolidinones may proceed slowly during an initial period during which the catalyst becomes activated. This catalyst activation period may take from as little as 5 minutes to several hours. The activation of the catalyst is typically indicated by an increase in temperature in the reactor as the isocyanates start to be consumed. Once the catalyst becomes activated, the polymerization tends to proceed rapidly.

According to embodiments, the amount of multi metal cyanide compounds in the reactive mixture is preferably from 5 to 5000 parts by weight per million (ppm) parts by weight of the reactive mixture. A preferred amount is at least 10 ppm, up to about 500 ppm. A more preferred amount is from 25 to 200 ppm.

According to embodiments, the process for making oxazolidinone compounds thereby using the oxazolidinone catalyst composition according to the invention is performed by combining the catalyst composition, the isocyanate composition and the epoxide composition and this may be performed in various ways selected from step-wise, continuous or semi-continuous.

The isocyanate composition is preferably added to the epoxide composition in a continuous or step-wise manner with two or more individual addition steps in the step-wise addition wherein in each individual addition step the amount of isocyanate compound added is <50 weight-% of the total amount of isocyanate compound to be added. This is to be understood in such a way that during the course of the reaction the isocyanate compound is added to the reaction mixture containing the epoxide compound continuously or in the aforementioned step-wise manner. Included is also the case that the isocyanate compound is added via a syringe pump, dripping funnel or other continuous or semi-continuous devices where the isocyanate is brought into the reaction mixture. Although some after-reaction time may be given to the reaction system, the reaction should be essentially complete shortly after the end of the addition of the isocyanate compound.

In one embodiment of the method according to the invention, the isocyanate composition is added continuously to the reaction mixture. "Continuously" in the meaning of the invention means that the isocyanate compound is added to the reaction mixture over a defined period of time, while at the same time any isocyanate compound present in the reaction mixture is converted to the oxazolidinone compound. Preferably, the rate of isocyanate addition is smaller than or equal to the maximum rate, with which the isocyanate compound can be converted under these reaction conditions to the oxazolidinone compound in order to avoid accumulation of NCO groups in the reaction mixture. The actual concentration of NCO groups in the reaction mixture may be observed, for example, by in-situ IR spectroscopy. If the NCO group concentration is observed to increase above a set value, the rate of isocyanate addition is reduced. Preferably, the isocyanate compound is added to the reaction mixture (comprising the isocyanate composition, the epoxide composition and the oxazolidinone catalyst of the invention) with such an addition rate that the concentration of the isocyanate compound in the reaction mixture is <40 wt %, preferably <20 wt % and more preferred<15 wt % calculated on the total weight of the reaction mixture, any solvent present not calculated.

In another embodiment of the method according to the invention, the amount of isocyanate compounds added in each individual addition step is >0.1 wt % to <50 wt % of the total amount of isocyanate compounds to be added. Preferably, the amount of isocyanate compound added per individual addition step is >1 wt % to <40 wt %, more preferred>5 wt % to <35 wt % of the total amount of isocyanate compound to be added. Preferably, the time intervals between each individual addition of isocyanate compound to the reaction mixture (comprising the isocyanate composition, the epoxide composition and the oxazolidinone catalyst of the invention) is chosen in such a way that the concentration of the isocyanate compounds in the reaction mixture at any given point in time is <40 wt %, preferably <20 wt % and more preferred<15 wt %. The actual concentration of NCO groups in the reaction mixture may be observed, for example, by in-situ IR spectroscopy. If the NCO group concentration is observed to increase above a set value, the time interval between the addition steps is increased.

The ratio of isocyanate compounds to epoxide compounds to be used in the reactive mixture is dependent upon the type of oxazolidinone compound and/or oxazolidinone comprising material desired. The ratio, however, may range from about 3:0.1 to about 0.1:3 isocyanate (NCO) equivalents to epoxide equivalents (NCO:epoxide), preferably in the range from about 3:1 to about 1:3 isocyanate (NCO) equivalents to epoxide equivalents (NCO:epoxide).

When oxazolidinone intermediate materials containing one or a multiple of oxazolidinone groups and unreacted isocyanate groups are desired, a compound or mixture of compounds having a plurality of isocyanate groups are reacted with a compound or mixture of compounds having a plurality of epoxide groups by the process of this invention in proportions such that the NCO:epoxide ratio is greater than 1:1.

When oxazolidinone intermediate materials products containing one or a multiple of oxazolidinone groups and unreacted epoxide groups are desired, a compound or mixture of compounds having a plurality of isocyanate groups are reacted with a compound or mixture of compounds having a plurality of epoxide groups by the process of this invention in proportions such that the NCO:epoxide ratio is less than 1:1.

When products containing a plurality of oxazolidinone groups and no unreacted isocyanate groups and no epoxide groups are desired, a compound or mixture of compounds containing a plurality of isocyanate groups is reacted with a compound or a mixture of compounds containing a plurality of vicinal epoxide groups by the process of this invention in proportions such that the NCO:epoxide ratio is about 1:1.

According to embodiments, the epoxide compounds used are preferably selected from any epoxy resin which is liquid at 20° C.

Examples of suitable mono-epoxide compounds are ethylene oxide, propylene oxide, 1,2-butene oxide, 2,3-butene oxide, butadiene mono-epoxide, 1,2-hexene oxide, cyclohexene oxide, vinylcyclohexene monoxide, limonene monoxide, oxides of C10-C18 alpha-olefins, styrene oxide, the epoxides of unsaturated fatty acid CI-CI 8 alkyl esters, methyl glycidyl ether, ethyl glycidyl ether, propyl glycidyl ether, butyl glycidyl ether, pentyl glycidyl ether, hexyl glycidyl ether, cyclohexyl glycidyl ether, octyl glycidyl ether, 2-ethylhexyl glycidyl ether, CIO-CI 8 alkyl glycidyl ether, allyl glycidyl ether, benzyl glycidyl ether, phenyl glycidyl ether, 4-tert-butylphenyl glycidyl ether, 1-naphthyl glycidyl ether, 2-naphthyl glycidyl ether, 2-chlorophenyl glycidyl ether, 4-chlorophenyl glycidyl ether, 4-bromophenyl glycidyl ether, 2,4,6-trichlorophenyl glycidyl ether, 2,4,6-tribromophenyl glycidyl ether, pentafluorophenyl glycidyl ether, o-cresyl glycidyl ether, m-cresyl glycidyl ether, p-cresyl glycidyl ether, glycidyl acetate, glycidyl cyclohexylcarboxylate, glycidyl benzoate, and N-glycidyl phthalimide. Preferred mono-epoxide compounds are ethylene oxide, propylene oxide, 1,2-butene oxide, 2,3-butene oxide, styrene oxide, butyl glycidyl ether, benzyl glycidyl ether, phenyl glycidyl ether, p-tolyl glycidyl ether, 4-tert-butylphenyl glycidyl ether.

A mixture of the aforementioned mono-epoxide compounds can also be used.

Diepoxide compounds are for example butadiene diepoxide, vinylcyclohexene diepoxide, limonene diepoxide, the diepoxides of double unsaturated fatty acid CI-CI 8 alkyl esters, ethylene glycol diglycidyl ether, di(ethylene glycol) diglycidyl ether, poly(ethylene glycol) diglycidyl ether, propylene glycol diglycidyl ether, di(propylene glycol) diglycidyl ether, poly(propylene glycol) diglycidyl ether, neopentyl glycol diglycidyl ether, polybutadiene diglycidyl ether, 1,6-hexanediol diglycidyl ether, hydrogenated bisphenol-A diglycidyl ether, 1,2-dihydroxybenzene diglycidyl ether, resorcinol diglycidyl ether, 1,4-dihydroxybenzene diglycidyl ether, bisphenol-A diglycidyl ether, diglycidyl ethers of polybutadiene-bisphenol-A-block-copolymers, diglycidyl o-phthalate, diglycidyl isophthalate, diglycidyl terephthalate.

Preferred di-epoxide compounds are butadiene di-epoxide, the di-epoxides of double unsaturated fatty acid C1-C18 alkyl esters, ethylene glycol diglycidyl ether, di(ethylene glycol) diglycidyl ether, poly(ethylene glycol) diglycidyl ether, propylene glycol diglycidyl ether, di(propylene glycol) diglycidyl ether, poly(propylene glycol) diglycidyl ether, neopentyl glycol diglycidyl ether, 1,6-hexanediol diglycidyl ether, hydrogenated bisphenol-A diglycidyl ether, 1,2-dihydroxybenzene diglycidyl ether, resorcinol diglycidyl ether, 1,4-dihydroxybenzene diglycidyl ether, bisphenol-A diglycidyl ether, diglycidyl o-phthalate, diglycidyl isophthalate, diglycidyl terephthalate.

A mixture of two or more the aforementioned di-epoxides can also be used. Polyepoxide compounds are for example glycerol polyglycidyl ether, trimethylolpropane polyglycidyl ether, pentaerythritol polyglycidyl ether, diglycerol polyglycidyl ether, polyglycerol polyglycidyl ether, sorbitol polyglycidyl ether. A mixture of one or more polyepoxide compounds and/or one or more of the aforementioned di-epoxide compounds can also be used.

According to embodiments, the isocyanate compounds are preferably selected from organic isocyanates containing a plurality of isocyanate groups including aliphatic isocyanates such as hexamethylene diisocyanate and more preferably aromatic isocyanates such as m- and p-phenylene diisocyanate, tolylene-2,4- and 2,6-diisocyanates, diphenylmethane-4,4'-diisocyanate, chlorophenylene-2,4-diisocyanate, naphthylene-1,5-diisocyanate, diphenylene-4,4'-diisocyanate, 4,4'-diisocyanate-3,3'-dimethyldiphenyl, 3-methyldiphenylmethane-4,4'-diisocyanate and diphenyl ether diisocyanate, cycloaliphatic diisocyanates such as cyclohexane-2,4- and 2,3-diisocyanates, 1-methyl cyclohexyl-2,4- and 2,6-diisocyanates and mixtures thereof and bis-(isocyanatocyclohexyl-)methane and triisocyanates such as 2,4,6-triisocyanatotoluene and 2,4,4'-triisocyanatodiphenyl ether.

According to embodiments, the isocyanate composition may comprise mixtures of polyisocyanates. For example a mixture of tolylene diisocyanate isomers such as the commercially available mixtures of 2,4- and 2,6-isomers and also the mixture of di- and higher poly-isocyanates produced by phosgenation of aniline/formaldehyde condensates. Such mixtures are well-known in the art and include the crude phosgenation products containing mixtures of methylene bridged polyphenyl polyisocyanates, including diisocyanate, triisocyanate and higher polyisocyanates together with any phosgenation by-products.

Preferred isocyanate compositions of the present invention are those wherein the polyisocyanate compounds are selected from an aromatic diisocyanate or polyisocyanate of higher functionality in particular crude mixtures of methylene bridged polyphenyl polyisocyanates containing diisocyanates, triisocyanate and higher functionality polyisocyanates. Methylene bridged polyphenyl polyisocyanates (e.g. Methylene diphenyl diisocyanate, abbreviated as MDI) are well known in the art and have the generic formula IV wherein n is one or more and in the case of the crude mixtures represents an average of more than one. They are prepared by phosgenation of corresponding mixtures of polyamines obtained by condensation of aniline and formaldehyde.

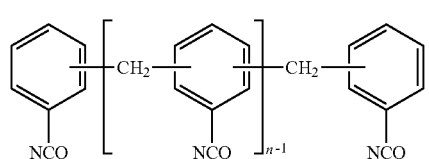

(IV)

Other suitable isocyanate compositions may include isocyanate ended prepolymers made by reaction of an excess of a diisocyanate or higher functionality polyisocyanate with a hydroxyl ended polyester or hydroxyl ended polyether and products obtained by reacting an excess of diisocyanate or higher functionality polyisocyanate with a monomeric polyol or mixture of monomeric polyols such as ethylene glycol, trimethylol propane or butane-diol. One preferred class of isocyanate-ended prepolymers is the isocyanate ended prepolymers of the crude mixtures of methylene bridged polyphenyl polyisocyanates containing diisocyanates, triisocyanates and higher functionality polyisocyanates.

According to embodiments, the isocyanate compounds in the isocyanate composition are selected from a toluene diisocyanate, a methylene diphenyl diisocyanate or a polyisocyanate composition comprising a methylene diphenyl diisocyanate or a mixture of such polyisocyanates.

The present invention further relates to oxazolidinone comprising materials made using the process according to the invention and making use of the oxazolidinone catalyst disclosed in the present invention (see formula I) and the use of said material. In particular this may include the use as building blocks in polyurethane based chemistry (or epoxy based chemistry). Possible application may include the use in composite materials, the use in high temperature stable materials, the use in thermoplastic materials (e.g. use as additives in Thermoplastic Polyurethanes (TPU)), Use in footwear applications, the use in elastomers, the use in cables & wires applications, the use in coatings, the use in electronic components, the use in encapsulants . . . .

FIGURES

FIG. 1 illustrates the Infrared spectrum for an oxazolidinone comprising materials made using the process according to the invention making use of the oxazolidinone catalyst disclosed in the present invention at different reaction temperatures, 156° C. and 90° C.

EXAMPLES

Chemicals Used:
  Suprasec® 3056 polyisocyanate ex Huntsman, in the examples indicated as S3056
  Araldite® DY-D/CH epoxide compound
  $Zn_3[Co(CN)_6]_2.2L.2H_2O$, in the examples indicated as DMC
  Cyclohexyltriphenylphosphonium bromide, $C_{24}H_{26}BrP$ (comparative catalyst)
  Suprasec® and Araldite® are trademarks of the Huntsman Corporation or an Affiliate thereof and have been registered in one or more but not all countries. The DMC catalyst used is ordered from Hongkong Huarun Int'l Industrial Co., LTD. The comparative catalyst, $C_{24}H_{26}BrP$ is ordered from VWR International.

Preparation of DMC Catalyst
  The catalyst is dried under vacuum in a rotating drying flask. The vacuum is gradually built up. Once the vacuum (15 mbar) is reached, the temperature can be built up gradually with a maximum temperature of 50° C. After 4 hours the oven will cool down to room temperature under vacuum conditions. After the oven is cooled down, the vacuum will be interrupted with nitrogen inlet and the catalyst can be taken out under nitrogen environment.

Preparation of Oxazolidinone Comprising Material

A three neck reaction flask equipped with mechanical stirrer, thermometer, reflux condenser and nitrogen inlet is used. An oil bath is used as heating source. Araldite® DY-D/CH is weight into the three neck flask. When the desired temperature is reached, the dry catalyst is loaded into the flask. Followed by a slow addition (1 gram/minute) of S3056 into the flask. When the addition is completed, the cook time starts and samples are taken on regular times and analysed by infrared spectroscopy and nuclear magnetic resonance spectroscopy.

Analyses

The composition of the reaction mixture was followed with a Bruker Tensor 27 spectrometer (average of 16 scans). The spectra were analysed with the software OPUS.

The 13C-NMR measurements were recorded on a Bruker 500 MHz Avance III spectrometer, operated at a frequency of 125.77 MHz. The experiments were carried out on 50% (w/w) solutions in acetone-d6, at ambient temperature in 10 mm NMR glass tubes spinning at circa 20 Hz. For 13C-NMR an inverse gated 1H-decoupling pulse program was used in combination with a pulse delay of 12.6 seconds, in order to make sure that all carbon nuclei were fully relaxed to their equilibrium states.

|  | Example No | | | | Comparative No | |
| --- | --- | --- | --- | --- | --- | --- |
|  | 1 | 2 | 3 | 4 | 1 | 2 |
| Composition |  |  |  |  |  |  |
| Ratio Araldite DY-D/CH-S3056 | 2.5/1 | 1.7/1 | 1.4/1 | 2.5/1 | 2.5/1 | 2.5/1 |
| DMC catalyst, ppm | 34 | 30 | 28 | 34 | 0 | 0 |
| $C_{24}H_{26}BrP$ catalyst, ppm | 0 | 0 | 0 | 0 | 0 | 34 |
| Process conditions |  |  |  |  |  |  |
| Temperature, ° C. | 156 | 145 | 145 | 90 | 150 | 156 |
| Cook time (min) | 5 | 5 | 5 | 60 | 40 | 40 |
| Characteristics C-NMR |  |  |  |  |  |  |
| ✓ Oxazolidinone (%)(*) | 100 | 100 | 100 | 8.6 | 86.9 | 85.2 |
| ✓ Isocyanurate (%)(**) | 0 | 0 | 0 | 91.4 | 13.1 | 14.8 |

(*)% = oxazolidinones/(oxazolidinones + isocyanurates) * 100%,
(**)% = isocyanurates/(oxazolidinones + isocyanurates) * 100%

Example 1

To a suitable flask equipped with a stirrer, temperature control, reflux condenser and nitrogen purge was charged 70.8 gram of 121 equivalent weight Araldite DY-D/CH. The glass flask was immersed into an oil bath and heated to 156° C. under stirring. When temperature is reached, 34 ppm DMC catalyst (calculated on total weight) is loaded into the flask. Subsequently, 29.2 gram S3056 was loaded stepwise with a pipet into the reaction mixture. From this moment, the cook time starts. A sample was taken after a cook time from 5 minutes and analyzed by infrared spectroscopy and nuclear magnetic resonance spectroscopy. This test indicates the formation of oxazolidinone rings, the complete disappearance of the isocyanate groups and the absence of isocyanurate groups.

Example 2

This experiment is repeated according to the procedure described in example 1 except 30 ppm DMC catalyst and 43.27 gram S3056 was loaded into the reaction mixture.

A sample was analyzed by infrared spectroscopy and nuclear magnetic resonance spectroscopy. This test indicates the formation of oxazolidinone rings, the complete disappearance of the isocyanate groups and the absence of isocyanurate groups.

Example 3

This experiment is repeated according to the procedure described in example 1 except 28 ppm DMC catalyst and 51.03 gram S3056 was loaded into the reaction mixture. A sample was analyzed by infrared spectroscopy and nuclear magnetic resonance spectroscopy. This test indicates the formation of oxazolidinone rings, the complete disappearance of the isocyanate groups and the absence of isocyanurate groups.

Example 4

This experiment is repeated with the same procedure as example 1 except now a process temperature of 90° C. is applied. A sample was taken after a cook time from 5 minutes and 60 minutes and analyzed by infrared spectroscopy. This test indicates the formation of significant quantities of isocyanurate groups and formation of oxazolidinone. Nuclear magnetic resonance spectroscopy verifies the existence of high quantities of isocyanurate groups.

Comparative 1:

This experiment is repeated according to the procedure described in example 1 except 0 ppm DMC catalyst was loaded. A sample was taken after a cook time from 40 minutes and analyzed by nuclear magnetic resonance spectroscopy. This test indicates the formation of oxazolidinone groups and the formation of isocyanurate groups.

Comparative 2:

This experiment is repeated according to the procedure described in example 1 except 34 ppm $C_{24}H_{26}BrP$ catalyst was loaded instead of DMC catalyst. A sample was taken after a cook time from 40 minutes and analyzed by nuclear magnetic resonance spectroscopy. This test indicates the formation of oxazolidinone groups and the formation of isocyanurate groups.

The invention claimed is:

1. A method for the production of oxazolidinone compounds, said method comprising combining and mixing at a temperature in the range 130-200° C. at least following compounds to form a reactive mixture:
    an isocyanate composition comprising at least one isocyanate compound;
    an epoxide composition comprising at least one epoxide compound;
    an oxazolidinone catalyst composition comprising at least an oxazolidinone catalyst compound selected from multi metal cyanide compounds corresponding to the formula

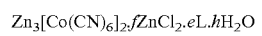

$$Zn_3[Co(CN)_6]_2 \cdot fZnCl_2 \cdot eL \cdot hH_2O \qquad [II]$$

wherein
    L=tBuOH or 1,2-dimethoxyethane
    e is the coordination number of the ligand or 0,
    f is a fraction or integer greater than or equal to 0, and
    h is a fraction or integer greater than or equal to 0.

2. The method according to claim 1, wherein the temperature is from 135 to 160° C.

3. The method according claim 1, wherein the amount of multi metal cyanide compounds in the reactive mixture is from 5 to 5000 parts by weight per million (ppm) parts by weight of the reactive mixture.

4. The method according to claim 1, wherein the isocyanate composition is added to the epoxide composition in a continuous or step-wise manner with two or more individual addition steps in the step-wise addition.

5. The method according to claim 1, wherein the isocyanate compounds in the isocyanate composition are selected from a toluene diisocyanate, a methylene diphenyl diisocyanate or a polyisocyanate composition comprising a methylene diphenyl diisocyanate or a mixtures thereof.

6. The method according to claim 3, wherein the amount of multi metal cyanide compounds in the reactive mixture is from 10 to 500 parts by weight per million (ppm) parts by weight of the reactive mixture.

7. The method according to claim 3, wherein the amount of multi cyanide compounds in the reactive mixture is from 25 to 200 ppm by weight per million (ppm) parts by weight of the reactive mixture.

\* \* \* \* \*